(12) United States Patent
Li et al.

(10) Patent No.: US 9,706,992 B2
(45) Date of Patent: Jul. 18, 2017

(54) SURGICAL STAPLER

(71) Applicant: B. J. ZH. F. Panther Medical Equipment Co., Ltd., Beijing (CN)

(72) Inventors: Xuejun Li, Beijing (CN); Qing Liu, Beijing (CN)

(73) Assignee: B. J. ZH. F. PANTHER MEDICAL EQUIPMENT CO., LTD., Beijing (CN)

(*) Notice: Subject to any disclaimer, the term of this patent is extended or adjusted under 35 U.S.C. 154(b) by 448 days.

(21) Appl. No.: 14/561,213

(22) Filed: Dec. 4, 2014

(65) Prior Publication Data

US 2015/0083779 A1 Mar. 26, 2015

Related U.S. Application Data

(63) Continuation of application No. PCT/CN2013/000667, filed on Jun. 4, 2013.

(30) Foreign Application Priority Data

Jun. 5, 2012 (CN) .......................... 2012 1 0181231

(51) Int. Cl.
| | |
|---|---|
| *A61B 17/068* | (2006.01) |
| *A61B 17/115* | (2006.01) |
| *A61B 17/10* | (2006.01) |
| A61B 17/29 | (2006.01) |
| A61B 90/00 | (2016.01) |

(52) U.S. Cl.
CPC .......... *A61B 17/068* (2013.01); *A61B 17/105* (2013.01); *A61B 17/1155* (2013.01); *A61B 2017/2946* (2013.01); *A61B 2090/0814* (2016.02)

(58) Field of Classification Search
CPC .............. A61B 17/068; A61B 17/1155; A61B 2017/2946

See application file for complete search history.

(56) References Cited

U.S. PATENT DOCUMENTS

| | | | | |
|---|---|---|---|---|
| 7,637,410 B2* | 12/2009 | Marczyk | .......... | A61B 17/07207 227/175.1 |
| 2012/0292371 A1* | 11/2012 | Nalagatla | ........... | A61B 17/1155 227/179.1 |
| 2013/0175319 A1* | 7/2013 | Felder | ................ | A61B 17/1155 227/175.2 |

* cited by examiner

*Primary Examiner* — Andrew M Tecco
(74) *Attorney, Agent, or Firm* — Matthias Scholl, PC; Matthias Scholl

(57) ABSTRACT

A surgical stapler, including: an anvil assembly, a reload assembly, a movable handle, a fixed handle, a transmission assembly, a propulsion assembly, a safety apparatus, and an anti-triggering device. The anti-triggering device includes two rows of holes and clamp strips. The transmission assembly is disposed inside the fixed handle. The clamp strips are arranged in longitudinal symmetry on one side of the anti-triggering device. A row of counterbores and a clamp plate having a structure matching with the clamp strip of the anti-triggering device are arranged at an inner side of the casing of the fixed handle. The safety apparatus is fixed at one side of the propulsion assembly. The anti-triggering device is clamped inside the casing of the fixed handle and is attached to a side surface of the safety apparatus.

10 Claims, 4 Drawing Sheets

SURGICAL STAPLER

CROSS-REFERENCE TO RELATED APPLICATIONS

This application is a continuation-in-part of International Patent Application No. PCT/CN2013/000667 with an international filing date of Jun. 4, 2013, designating the United States, now pending, and further claims priority benefits to Chinese Patent Application No. 201210181231.8 filed Jun. 5, 2012. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND OF THE INVENTION

Field of the Invention

The invention relates to a surgical stapler, and more particularly to a surgical stapler comprising an anti-secondary triggering mechanism.

Description of the Related Art

A typical circular stapler includes a manual outer safety device arranged at a movable handle for the purpose of avoiding unexpected triggering of the instrument. However, such a device is only designed for the prevention of misoperation of the instrument but cannot prevent secondary triggering. In addition, secondary use of the instrument leads in some cases to cross infections and increases the surgical risk.

SUMMARY OF THE INVENTION

In view of the above-described problems, it is one objective of the invention to provide a disposable stapler comprising an anti-secondary triggering mechanism which is disposed inside the instrument, matches with structures of the transmission assembly and the propulsion device, and is locked once the instrument is triggered, thereby preventing a secondary triggering.

To achieve the above objective, in accordance with one embodiment of the invention, there is provided a disposable surgical stapler comprising: an anvil assembly, a reload assembly, a movable handle, a fixed handle, a transmission assembly, a propulsion assembly, a safety apparatus, and an anti-triggering device. The fixed handle comprises a casing comprising a row of counterbores and clamp flats. The anti-triggering device comprises two rows of holes and clamp strips. The anvil assembly is disposed at a front end of the surgical stapler. A stapling gap is formed between the anvil assembly and the reload assembly. The transmission assembly is disposed inside the fixed handle. The clamp strips are arranged in longitudinal symmetry on one side of the anti-triggering device. The row of counterbores and the clamp plates are arranged at an inner side of the casing of the fixed handle. Each clamp plate has a structure matching with the clamp strip of the anti-triggering device. The safety apparatus is fixed at one side of the propulsion assembly. The anti-triggering device is clamped inside the casing of the fixed handle and is attached to a side surface of the safety apparatus.

In a class of this embodiment, the safety apparatus comprises a safety piece and a fixing block; and the safety piece is disposed inside the fixing block.

In a class of this embodiment, a left side of the safety piece comprises a convex strip, and a right side of the safety piece comprises three convex strips. The convex strip of the left side is in elastic contact with the transmission assembly via springs arranged inside the fixing block. The three convex strips of the right side press against the anti-triggering device.

In a class of this embodiment, compression springs are disposed between an upper convex strip and a lower convex strip of the right side of the safety piece and the anti-triggering device. The compression springs are provided with spring sheaths, respectively.

In a class of this embodiment, both a first row of holes and a second row of holes of the anti-triggering device comprise three holes in vertical arrangement. A middle hole of each of the first row and the second row has a size matching with a middle convex strip of the right side of the safety piece. An upper hole and a lower hole of the first row have sizes smaller than sizes of an upper hole and a lower hole of the second row, respectively.

In a class of this embodiment, the second row of holes arranged on the anti-triggering device have structures matching with a middle convex strip of the right side of the safety piece and spring sheaths disposed on the safety piece.

In a class of this embodiment, the anti-triggering device is disposed on a surface of the fixing block attached to one side of the fixed handle.

In a class of this embodiment, the anti-triggering device further comprises a convex part.

In a class of this embodiment, an ejector sleeve is provided with a neck matching with a convex part of the anti-triggering device.

In a class of this embodiment, the anti-triggering device is a metal material having elasticity.

Advantages according to embodiments of the invention are summarized as follows:

The disposable surgical stapler comprises the anti-secondary triggering mechanism and is adapted to preventing tissue cross infection resulting from a secondary use after the triggering. The stapler of the invention has a simple structure, convenient assembly, and safe use. The stapler is totally automatic and does not necessitate manual regulation, so that it is very significant in prevention of secondary triggering and is adapted to wide application.

BRIEF DESCRIPTION OF THE DRAWINGS

The invention is described hereinbelow with reference to the accompanying drawings, in which.

DETAILED DESCRIPTION OF THE EMBODIMENTS

For further illustrating the invention, experiments detailing a disposable surgical stapler comprising an anti-secondary triggering mechanism are described below. It should be noted that the following examples are intended to describe and not to limit the invention.

Figure 1:
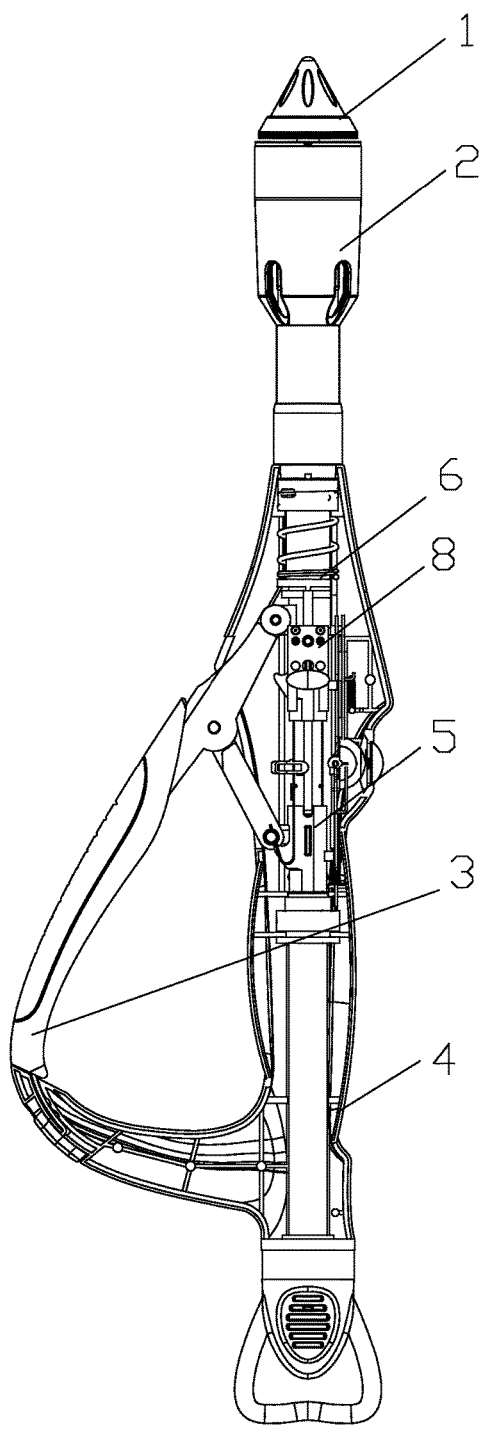
FIG. 1 is a schematic diagram of a surgical stapler comprising an anti-secondary triggering mechanism in accordance with one embodiment of the invention.
Figure 2:
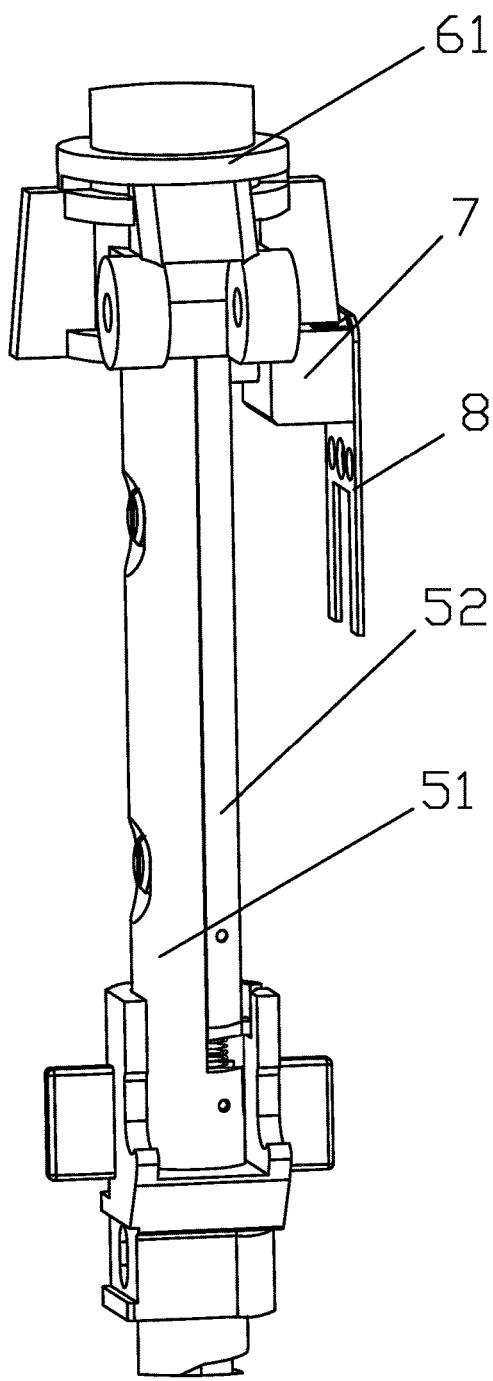
FIG. 2 is a schematic diagram showing a safety apparatus mounted inside a surgical stapler in accordance with one embodiment of the invention.
Figure 3:
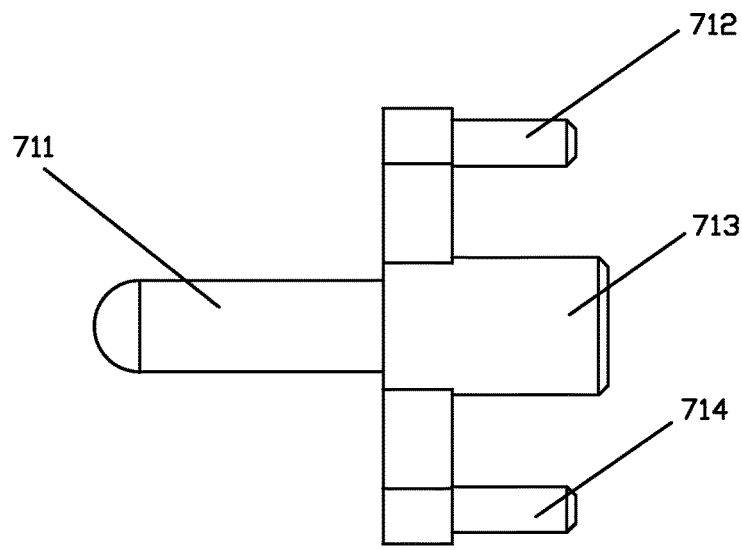
FIG. 3 is a schematic diagram of a safety piece in accordance with one embodiment of the invention.
Figure 4:
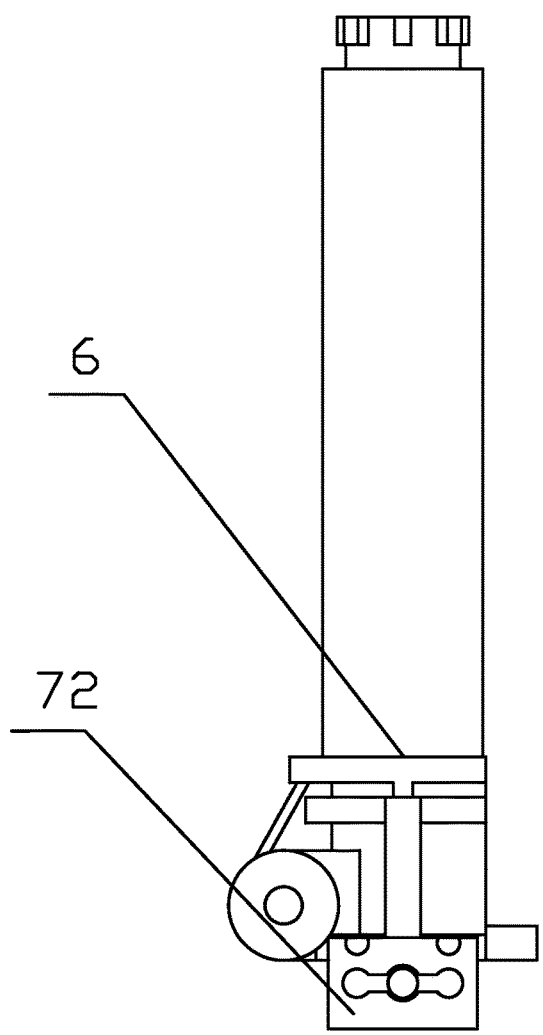
FIG. 4 is a schematic diagram showing an ejector sleeve fixed with a fixing block in accordance with one embodiment of the invention.
Figure 5:
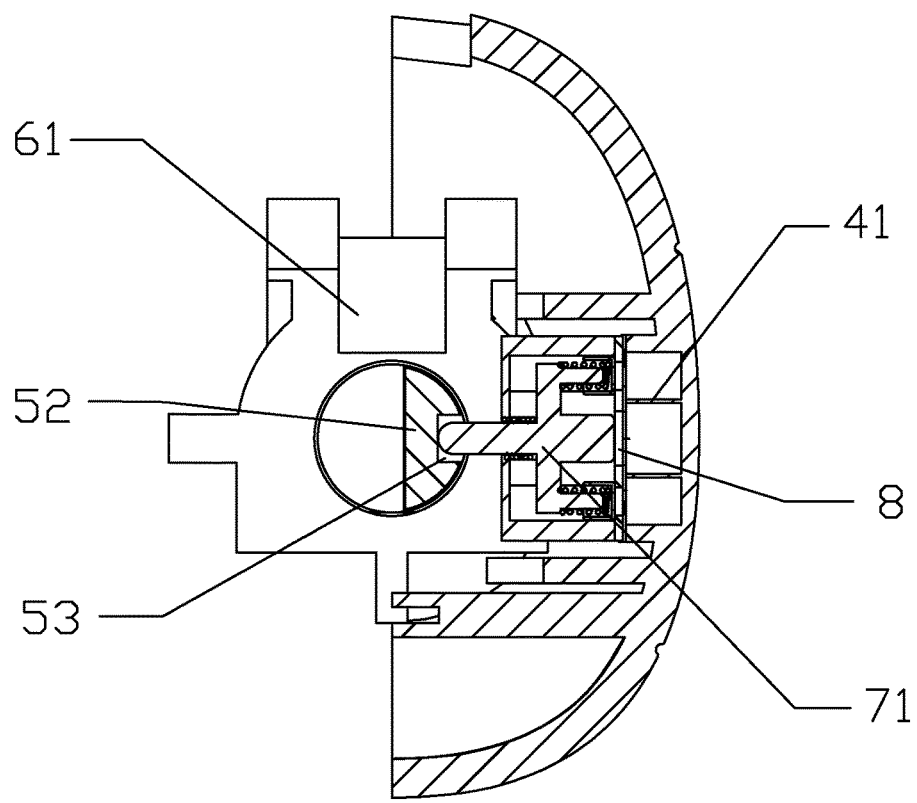
FIG. 5 is a cross sectional view of a safety apparatus inside a surgical stapler in accordance with one embodiment of the invention.

A surgical stapler, as shown in FIG. 1, comprises: an anvil assembly 1, a reload assembly 2 forming a stapling gap with the anvil assembly 1, a movable handle 3, a fixed handle 4, a transmission assembly 5 mounted inside the fixed handle 4, and a propulsion assembly 6 matching with the transmission assembly 5. The surgical stapler further comprises a safety apparatus 7 and an anti-triggering device 8.

As shown in FIGS. 2-5, the transmission assembly 5 comprises a screw rod 51 and a positioning connecting rod 52. The positioning connecting rod 52 is provided with a safety piece chute 53. A screw enables the positioning connecting rod 52 and the screw rod 51 to be in fixed connection and ensures slide fit between the positioning connecting rod 52 and the screw rod 51 when the screw is fastened. The safety apparatus 7 can be tightly attached to the safety piece chute 53 of the positioning connecting rod 52 and can move in relation to the safety piece chute 53. With the axial movement of the screw rod 51, the safety apparatus 7 moves along the chute 53 of the positioning connecting rod 52 at one side of a convex strip close to the operator in a direction perpendicular to the axial direction.

The safety apparatus 7 is disposed on an ejector sleeve 61 of the propulsion assembly 6 and is clamped in an inner cavity of a side of the fixed handle 3 within a proper interval. Specifically, the safety apparatus 7 is fixed at a proximal end of the ejector sleeve 61 of the propulsion assembly 6. The anti-triggering device 8 is clamped inside a casing of the fixed handle and is tightly attached to a side surface of the safety apparatus 7.

Preferably, the ejector sleeve 61 is provided with a pair of necks.

The safety apparatus 7 comprises a safety piece 71 and a fixing block 72. The safety piece 71 is mounted in an inner cavity of the fixing block 72. A left side of the safety piece 71 comprises a convex strip 711, and a right side of the safety piece 71 comprises three convex strips 712, 713, and 714. The convex strip 711 of the left side of the safety piece 71 is in elastic contact with the transmission assembly 5 by arranging compression springs 721 inside the fixing block 72. The three convex strips 712, 713, and 714 of the right side press the anti-triggering device 8.

To make sure that the convex strip 711 of the left side of the safety piece 71 always presses the chute 53 of the positioning connecting rod 52 and maintains in balance, two springs are symmetrically arranged in the left and the right of a central plane of the safety piece 71 at the convex strips of the right side so as to uniformly and stably press the safety piece 71 on the chute 53 of the positioning connecting rod 52. With the axial movement of the positioning connecting rod 52, the safety piece 71 moves in perpendicular to the axial direction along with the convex and concave variation of the surface of the chute 53 of the positioning connecting rod 52.

Preferably, the convex strips 711 of the left side of the safety piece 71 is designed to be a semi-sphere having a smooth surface so as to reduce a friction between the safety piece 71 and the positioning connecting rod 52 during the movement of the screw rod 51. The springs mounted on an upper convex strip 712 and a low convex strip 714 of the right side of the safety piece 71 are provided with spring sheaths so that the friction force between the two springs mounted on the right side of the safety piece and the anti-triggering device is prevented from being too large which otherwise results in locking of the two springs of the right side of the safety piece by the anti-triggering device.

Figure 6:
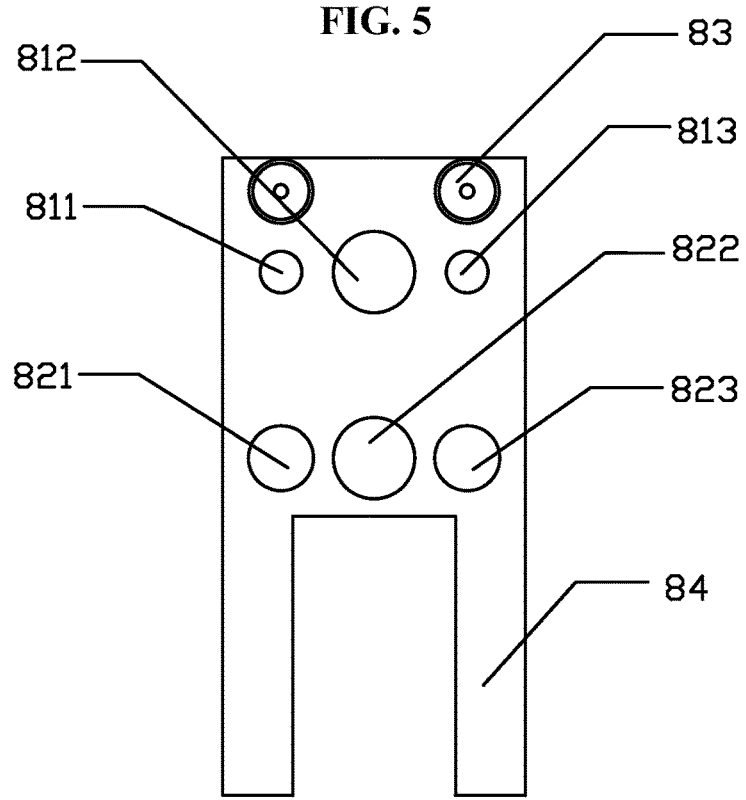
FIG. 6 is a schematic diagram of an anti-triggering device of an anti-secondary triggering mechanism in accordance with one embodiment of the invention.

As shown in FIG. 6, the anti-triggering device 8 is provided with convex parts 84 and two rows of holes. A side of the anti-triggering device 8 is provided with clamp strips 83 arranged in longitudinal symmetry.

Preferably, a first row of holes and a second row of holes of the anti-triggering device 8 are longitudinally arranged three holes, respectively. Two middle holes 812, 822 have sizes matching with a middle convex strip 713 of the right side of the safety piece 7, and both sizes of an upper hole 811 and a lower hole 813 of the first row are smaller than that of an upper hole 821 and a lower hole 823 of the second row. Structures of the second row of holes 821, 822, and 823 of the anti-trigger piece 8 match with the middle convex strip 713 of the right side of the safety piece and the spring sheaths of the safety piece 71.

Figure 7:
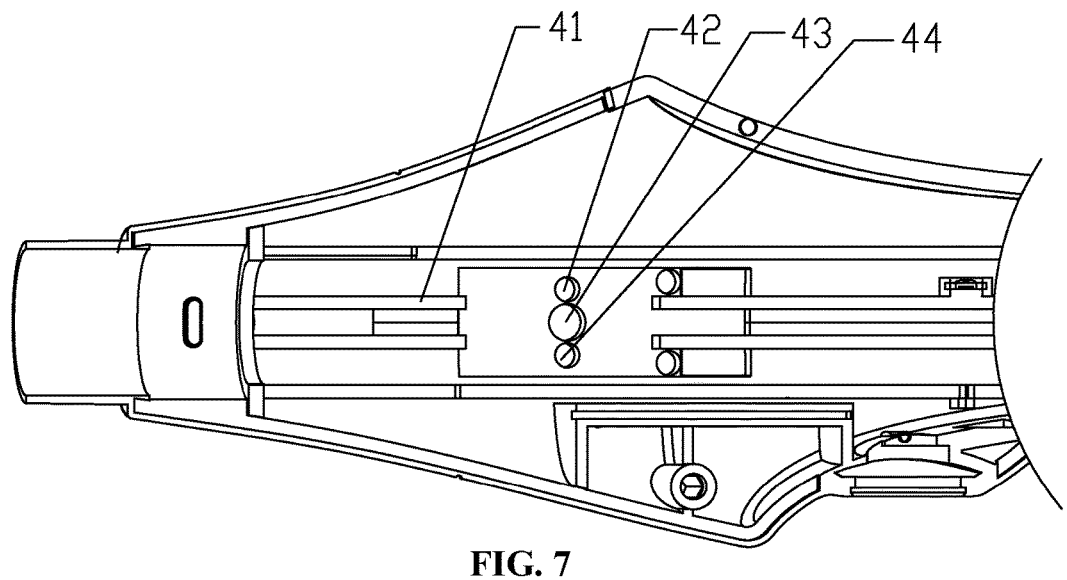
FIG. 7 is a schematic diagram showing a cavity of a fixed handle in accordance with one embodiment of the invention.

As shown in FIG. 7, an inner side of the casing of the fixed handle 4 is provided with a clamp plate 41 as well as three vertically arranged counterbores 42, 43, and 44.

When the anti-triggering device 8 and the ejector sleeve 61 are assembled and connected, the two convex parts 84 arranged on the anti-triggering device 8 are pressed into the necks arranged on the ejector sleeve 61. The necks are ⅗ semi-circular holes. When the surgical stapler is triggered, the movable handle 3 drives the ejector sleeve 61 to move in the axial direction away from the operator, the ejector sleeve 61 pushes the reload assembly 2, a titanium screw inside the reload assembly 2 perforates a tissue and is bent backwards when it reaches the anvil assembly 1, thereby finishing the surgery. Since the convex parts 84 disposed on the anti-triggering device 8 match with the necks of the ejector sleeve 61, the anti-triggering device 8 synchronously moves forward driven by the ejector sleeve 61 during the forward movement of the ejector sleeve 61.

When the trigger of the surgical stapler is finished and the movable handle 3 needs to return to the original state, the anti-triggering device 8 is disposed at a position locked by the clamp plate 41 arranged on the casing of the fixed handle 4, thereby being unable to be reset. The anti-triggering device 8 knocks on the clamp plate 41 of the casing of the fixed handle 4. Because of a backward restoring force of the ejector sleeve 61, the necks of the ejector sleeve crack under the drive of the convex parts 84 of the anti-trigger piece 8, so that the anti-triggering device 8 is unable to return to the original position.

Figure 8:
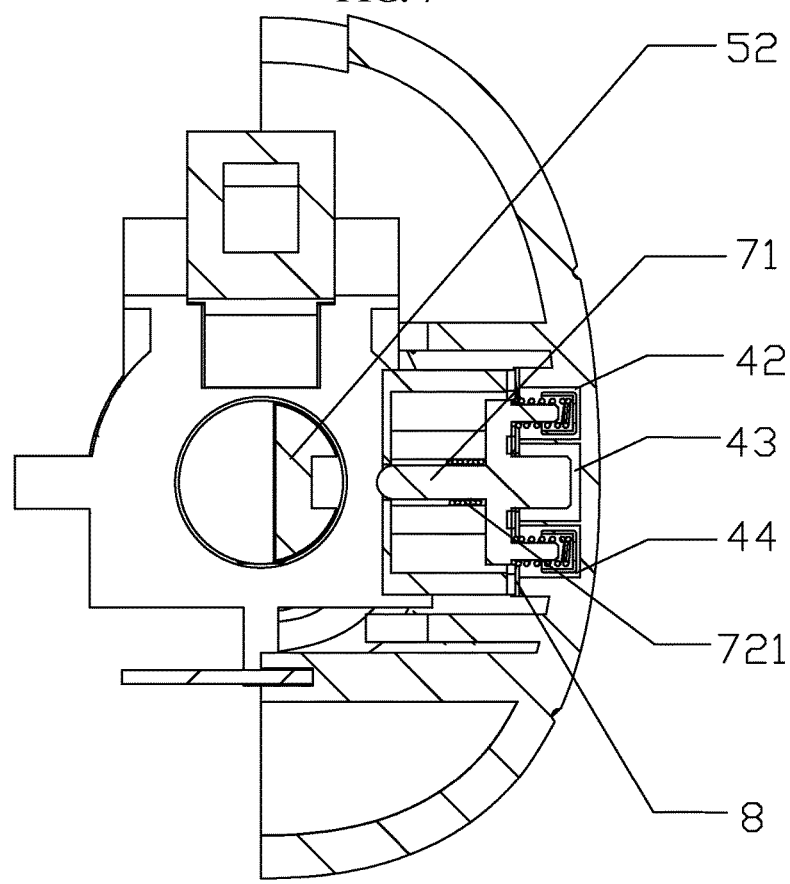
FIG. 8 is a cross section view of a stapler in a locked state after being triggered in accordance with one embodiment of the invention.

As shown in FIG. 8, when the anti-triggering device 8 is unable to return to an original position, positions of the second row of holes of the anti-triggering device 8 are corresponding to the positions of the three counterbores 41, 42, and 43 arranged on the casing of the fixed handle. The ejector sleeve 61 drives the safety apparatus 7 except the anti-triggering device 8 to return to the original position. A pressure from the right side of the safety piece 71 disappears, the spring sheaths and the middle convex strip 713 of the right side of the safety piece pass through the second row of holes 821, 822, and 823 of the anti-triggering device 8 and enter the counterbores 42, 43, and 44 arranged on the casing of the fixed handle 4 under the tension of the spring of the left side 721. Thus, the ejector sleeve 61 and the casing of the fixed handle 3 are locked together as a whole and cannot move in relation to each other. When the ejector sleeve 61 and the casing of the fixed handle 3 are locked together, the surgical stapler cannot be triggered for a second time.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A surgical stapler, comprising:
   a) an anvil assembly;
   b) a reload assembly;
   c) a movable handle;
   d) a fixed handle, the fixed handle comprising a casing comprising a row of counterbores and clamp flats;
   e) a transmission assembly;
   f) a propulsion assembly;
   g) a safety apparatus; and
   h) an anti-triggering device, the anti-triggering device comprising two rows of holes and clamp strips;
   wherein
   the anvil assembly is disposed at a front end of the surgical stapler;
   a stapling gap is formed between the anvil assembly and the reload assembly;
   the transmission assembly is disposed inside the fixed handle;
   the clamp strips are arranged in longitudinal symmetry on one side of the anti-triggering device;
   the row of counterbores and the clamp plates are arranged at an inner side of the casing of the fixed handle;
   each clamp plate has a structure matching with the clamp strip of the anti-triggering device;
   the safety apparatus is fixed at one side of the propulsion assembly; and
   the anti-triggering device is clamped inside the casing of the fixed handle and is attached to a side surface of the safety apparatus.

2. The stapler of claim 1, wherein the safety apparatus comprises a safety piece and a fixing block; and the safety piece is disposed inside the fixing block.

3. The stapler of claim 2, wherein
   a left side of the safety piece comprises a convex strip, and a right side of the safety piece comprises three convex strips;
   the convex strip of the left side is in elastic contact with the transmission assembly via springs arranged inside the fixing block; and
   the three convex strips of the right side press against the anti-triggering device.

4. The stapler of claim 3, wherein
   compression springs are disposed between an upper convex strip and a lower convex strip of the right side of the safety piece and the anti-triggering device; and
   the compression springs are provided with spring sheaths, respectively.

5. The stapler of claim 1, wherein
   both a first row of holes and a second row of holes of the anti-triggering device comprise three holes in vertical arrangement;
   a middle hole of each of the first row and the second row has a size matching with a middle convex strip of the right side of the safety piece; and
   an upper hole and a lower hole of the first row have sizes smaller than sizes of an upper hole and a lower hole of the second row, respectively.

6. The stapler of claim 1, wherein a second row of holes are arranged on the anti-triggering device and have structures matching with a middle convex strip of a right side of the safety piece and spring sheaths disposed on the safety piece.

7. The stapler of claim 1, wherein the anti-triggering device is disposed on a surface of the fixing block attached to one side of the fixed handle.

8. The stapler of claim 1, wherein the anti-triggering device further comprises a convex part.

9. The stapler of claim 1, wherein an ejector sleeve is provided with a neck matching with a convex part of the anti-triggering device.

10. The stapler of claim 1, wherein the anti-triggering device is a metal material having elasticity.

\* \* \* \* \*